United States Patent [19]
Halaka

[11] Patent Number: 6,071,480
[45] Date of Patent: *Jun. 6, 2000

[54] METHOD FOR GENERATING A STANDING SONIC WAVE, METHODS OF SONICATION WITH A STANDING SONIC WAVE, AND A STANDING SONIC WAVE SONICATOR

[75] Inventor: Folim G. Halaka, Waukegan, Ill.

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/564,995

[22] Filed: Dec. 21, 1995

Related U.S. Application Data

[63] Continuation-in-part of application No. 08/362,640, Dec. 22, 1994, abandoned.

[51] Int. Cl.[7] .............................. B06B 1/00; C12N 13/00; C12M 1/33
[52] U.S. Cl. .................... 422/128; 435/173.7; 435/306.1
[58] Field of Search .............................. 435/173.7, 306.1; 422/20, 128; 128/200.16; 204/157.62

[56] References Cited

U.S. PATENT DOCUMENTS

| | | | |
|---|---|---|---|
| 4,571,087 | 2/1986 | Ranney | 366/108 |
| 4,874,137 | 10/1989 | Chiba | 241/301 |
| 4,983,523 | 1/1991 | Li et al. | 435/173.7 |
| 5,005,773 | 4/1991 | Nyberg et al. | 241/30 |
| 5,074,474 | 12/1991 | Golz et al. | 241/1 |
| 5,180,363 | 1/1993 | Idemoto et al. | 604/22 |
| 5,374,522 | 12/1994 | Murphy et al. | 435/6 |
| 5,386,169 | 1/1995 | Dubruque | 310/323 |

FOREIGN PATENT DOCUMENTS

| | | |
|---|---|---|
| 0288618 | 11/1988 | European Pat. Off. . |
| 0337690 | 10/1989 | European Pat. Off. . |
| 0394583 | 10/1990 | European Pat. Off. . |
| 0520756 | 12/1992 | European Pat. Off. . |
| 0619147 | 10/1994 | European Pat. Off. . |
| 938163 | 10/1963 | United Kingdom . |
| 9212807 | 8/1992 | WIPO . |
| 9603150 | 2/1993 | WIPO . |
| 9413783 | 6/1994 | WIPO . |

OTHER PUBLICATIONS

Fisher 88 Catalog (1988) pp. 724–725 and 973–977.
Bass, Jr., J., "Diagnostic Standards and Classification of Tuberculosis", *Am. Rev. Respir. Dis.*, 142:725–735 (1990).

*Primary Examiner*—Jon P. Weber
*Attorney, Agent, or Firm*—Paul D. Yasger

[57] ABSTRACT

The present invention provides a standing sonic wave sonicator, methods of generating a standing sonic wave and a method of sonication which employs a standing sonic wave to disrupt particulate material.

13 Claims, 4 Drawing Sheets

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:1:

AACCTGTGGG GTCCGGCCTT TCACGAGAGG TATCCGAACG TCAC        44

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:2:

AACCTGTGGG GTCCGGCCTT T        21

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:3:

GGCCGGACCC CACAGGTT        18

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:4:

GAGAGGTATC CGAACGTCAC        20

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear -continued (ii) MOLECULE TYPE: synthetic DNA (xi) SEQUENCE DESCRIPTION: SEQ ID NO:5:

GTGACGTTCG GATACCTCTC GTG                                    23

METHOD FOR GENERATING A STANDING SONIC WAVE, METHODS OF SONICATION WITH A STANDING SONIC WAVE, AND A STANDING SONIC WAVE SONICATOR

This application is a continuation-in-part of co-pending U.S. patent application Ser. No. 08/362,640, filed Dec. 22, 1994, now abandoned, the entirety of which is herein incorporated by reference.

FIELD OF THE INVENTION

The present invention relates to sonic waves and in particular relates to generating ultrasonic waves which can be used to sonicate particulate material.

BACKGROUND OF THE INVENTION

Ultrasonic energy is used in a variety of industrial and scientific areas to disrupt or otherwise break apart particulate material ranging from sewage to microorganisms such as viruses or bacteria. The manner in which ultrasonic energy or ultrasound disrupts solid materials has been described as the propagation of an ultrasonic sound wave in a medium which causes pressure changes within the medium. These pressure changes can be as great as 20,000 atmospheres and particulate material in the medium that is unable to withstand the pressure changes is disrupted.

"Sonicators" are devices which are used to disrupt particulate material using ultrasonic waves. Sonicators generally can be categorized into three categories. First, "immersion" sonicators typically involve dipping a vibrating probe which emits ultrasonic waves into a liquid sample. U.S. Pat. No. 5,074,474 describes an immersion type sonicator.

Second, "bath" sonicators generally comprise a container that vibrates and any liquid in the container is subject to ultra-sonic waves produced by the vibrating container. Typically, the container is filled with water and a sample contained in a second container is placed in the water. Accordingly, any solids in the sample container are subjected to ultrasonic energy. A bath type sonicator is disclosed in U.S. Pat. No. 4,874,137.

Last, "direct" sonicators apply ultrasonic energy directly to a vessel containing a sample. If present, particulate material present in the sample is subjected to ultrasonic energy. A direct sonicator is disclosed in U.S. Pat. No. 4,983,523.

SUMMARY OF THE INVENTION

The present invention provides a sonicator comprising an electrical wave generator, a vibrating element electrically connected to the electrical wave generator and a vibratable member transversley secured to the vibrating element. The sonicator can be employed to sonicate a test sample and the steps of such a method include (a) converting an electrical energy wave into a vibrational energy wave; (b) contacting a vibratable member with the vibrational energy wave to generate a standing sonic wave; and (c) contacting a test sample with the standing sonic wave to thereby sonicate any particulate or polymeric material in the test sample. Also provided is a method of generating a standing sonic wave across a vibratable member by propagating vibrational energy along a shaft to a vibratable member to thereby generate a standing sonic wave across the vibratable member.

DETAILED DESCRIPTION OF THE INVENTION

Applicant has observed that ultrasonic waves transmit across a vibratable member transversley secured to a source of vibrational energy. Additionally, the resulting wave across such a vibratable member can have a frequency higher than the frequency of the wave emitted from the source of vibrational energy. Applicant's invention is directed to creating such a wave across a vibratable member and sonicating particulate or polymeric material using the standing sonic wave.

Figure 1:
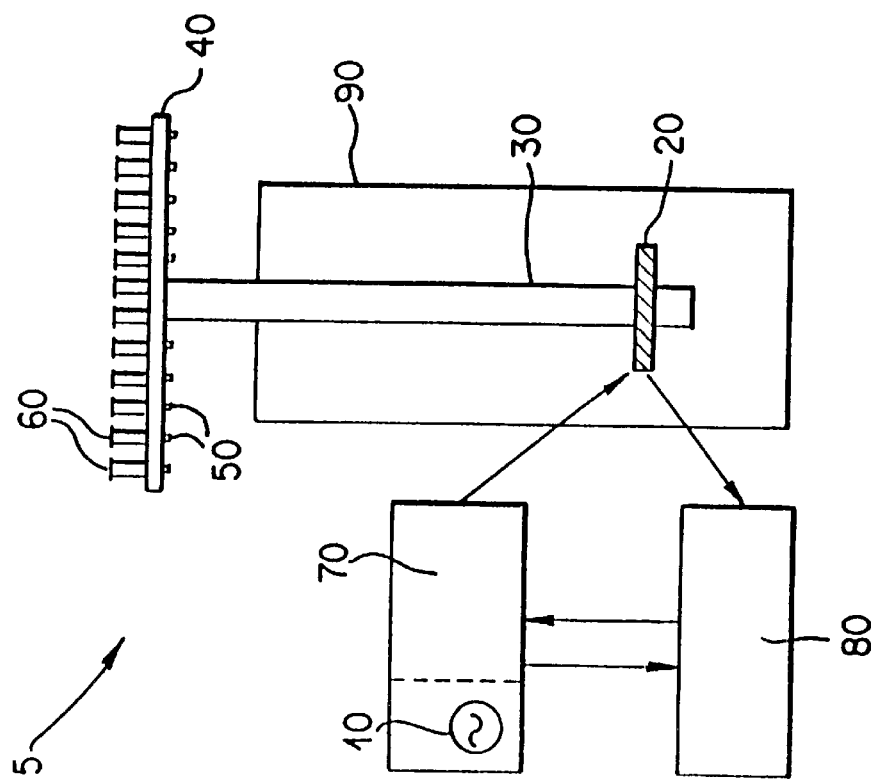

Standing sonic wave sonicator 5 is shown in FIG. 1. As shown by FIG. 1, electrical wave generator 10 is electrically connected to vibrating element 20. Shaft 30 projects through vibrating element 20 and transversley secures vibratable member 40 to vibrating element 20. While preferred, shaft 30 is not necessary as vibratable member 40 can be transversley secured to vibrating element 20 directly. Vibratable member 40 defines a plurality of apertures 50 which secure sample tubes 60 to vibratable member 40.

Figure 2:
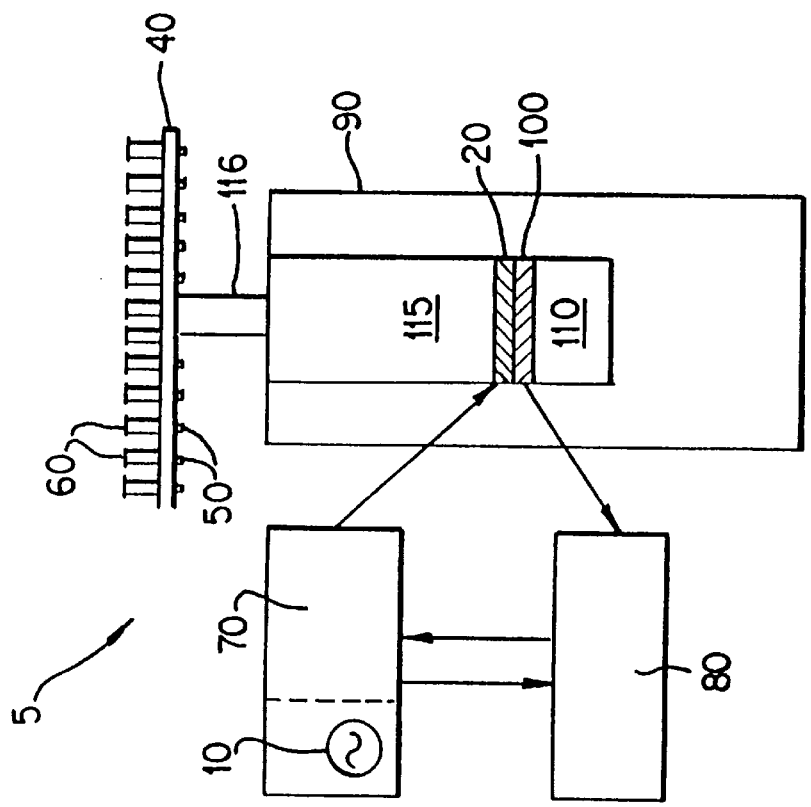
FIG. 1 and FIG. 2 schematically illustrate embodiments of a standing sonic wave sonicator according to the present invention.

Other components that can be employed with the electrical wave generator 10, vibrating element 20, shaft 30 and vibratable member 40 are shown in FIG. 1 and FIG. 2. Looking at FIG. 1, an amplifier 70 can be electrically connected to electrical wave generator 10 to amplify the electrical energy generated by electrical wave generator 10. Additionally, electrical wave generator 10 and vibrating element 20 can be operatively coupled to feedback phase tracking loop 80 which insures that any impedance experienced by vibrating element 20 is minimized. Housing 90 which surrounds vibrating element 20 and the majority of shaft 30 can be employed to enclose and insulate the components which they surround. A housing which surrounds the entire system (not shown) can also be employed to further diminish any sound (or radio frequency) emanating from the sonicator.

FIG. 2 illustrates an embodiment of the invention in which it is contemplated that multiple vibrating elements are employed. Typically, two vibrating elements are employed. FIG. 2, shows a first vibrating element 20 and a second vibrating element 100. According to this embodiment, vibrating element 100 is contacting the vibrating element 20 in a so-called "stacked" configuration where one vibrating element is aligned on top of the other. FIG. 2 also shows a preferred embodiment for transversely securing vibratable member 40 to vibrating elements 20 and 100. According to this embodiment, positioning sheaths 110 and 115, as well as shaft 116 are employed to secure vibratable member 40 to the vibrating elements. Positioning sheaths 110 and 115 sandwich vibrating elements 20 and 100. Positioning sheath 115 is further secured to shaft 116 which is in turn secured to vibratable member 40 to thereby secure it transversely to vibrating elements 20 and 100. Positioning sheath 110 buttresses vibrating elements 20 and 100 and positioning sheath 115 is employed, in concert with shaft 116, to convey vibrational energy to vibratable member 40. Other means for transversely securing a vibratable member to the vibrating element(s) include, but are not limited to welds, screws, pinion rods, flanges, and the like. The phrase "transversley securing" as used herein to describe the connection or orientation between a vibratable member and vibrating element means that the vibratable member is held in a position whereby a vibrational wave emitted by a vibrating element crosses or intersects the vibratable member.

Generally, sonicating a test sample with the sonicator provided herein is achieved by converting electrical energy into vibrational energy; transferring vibrational energy, either directly or indirectly, to a vibratable member; forming a standing sonic wave across the vibratable member; and contacting a sample tube with the standing sonic wave. A test sample in the sample tube is therefore subjected to the energy of the standing sonic wave and thereby sonicated. Test samples that may be sonicated as taught herein can be anything containing particulate material including but not limited to human and animal body fluids such as whole blood, serum, plasma, cerebrospinal fluid, urine, lymph fluids, ascites fluid, tears, saliva, sputum, milk and the like; as well as biological fluids such as cell culture supernatants.

Electrical wave generator 10 is the source of energy for the standing sonic wave sonicator. When electrical wave generator 10 is activated, it emits electrical energy in the form of a wave. Electrical wave generators are well known in the art and are sources of electrical energy waves that can be adjusted to have various wavelengths, amplitudes, voltages, currents and the like. Typically, the electrical wave output from the electrical wave generator has a frequency of between about 5 KHz and about 80 Khz and more typically between about 20 KHz and about 60 KHz. In cases where an amplifier is employed, the electrical wave can be transferred to the amplifier by electrically connecting the electrical wave generator with the amplifier.

Amplifier 70 may be electrically connected with electrical wave generator 10 using methodologies well known to those skilled in the art. When employed, amplifier 70 receives electrical energy in the form of a wave, from electrical wave generator 10. Amplifiers are also well known in the art and are typically employed to increase an electrical wave's energy. According to the present invention, increasing an electrical wave's energy typically does not effect the frequency, but increases a waves amplitude. Accordingly, an amplified wave has an increased voltage and current in comparison to the wave generated by electrical wave generator 10. While there are electrical wave generators that can output high energy waves, typically, a lower energy electrical wave from a electrical wave generator is amplified prior to its contact with the vibrating element.

An electrical wave produced by electrical wave generator 10, and when applicable, amplified by amplifier 70, is transferred to vibrating element 20 typically through connections and wires or other means for transferring electrical energy to the vibrating elements and therefore electrically connecting the amplifier with the vibrating elements.

A vibrating element is generally anything that changes electrical energy into mechanical or vibrational energy and transfers the vibrational energy, directly or indirectly, to the vibratable member. Piezoelectric substances are typically polarized crystalline materials which are well known in the art for their ability to transform electrical energy into mechanical energy. It is also known that piezoelectric materials emit vibrational waves in particular directions. Ceramic piezoelectric materials such as lead zirconium niobate are preferred.

Different piezoelectric materials are also known to have different "inherent frequencies". A piezoelectric materials inherent frequency is the frequency at which a piezoelectric material encounters the least impedance (or resistance) in converting electrical energy into vibrational energy. To avoid resistance, it is generally preferred that the frequency of an electrical energy wave that is transferred to a piezoelectric vibrating element is substantially the same as an inherent frequency of a piezoelectric material. Specifically, the frequency of the energy input is preferably within several Hz of the vibrating element's inherent frequency. Thus, if the inherent frequency of the vibrating element is 40 KHz, it would be preferable to generate an electrical energy wave having a frequency of between about 39.8 KHz and about 40.2 KHz, most preferably between about 39.94 KHz and about 40.01 KHz.

As previously mentioned, a plurality of vibrating elements can be employed according to the instant invention. When a plurality of piezoelectric vibrating elements are employed, they should be aligned such that the vibrational waves that they emit do not compress each other or diminish the effects of the waves that one or the others emit. In cases where the vibrating elements are stacked (i.e. contacting each other) those skilled in the art will recognize that the poles of the vibrating elements should be aligned such that positive poles are contacting each other and negative poles are at opposite ends of the stack. On the other hand, if multiple vibrating elements are not stacked, but are spaced from one another, they are preferably spaced from each other at locations on, for example, a shaft where the energy of the waves which they emit is at a minimum. These locations are primarily based upon the wavelength of the waves created by the vibrating elements.

Specifically, between the origin of a wave and a distance of one wavelength from the origin, a wave has three points of minimum energy. Graphically speaking, minimum energies occur at points where a wave crosses the axis which defines its direction of propagation. Assuming a wave begins at the axis which is perpendicular to the direction of the wave, the areas of minimum energy occur at the wave's origin, at one-half wavelength from the origin and at a full wavelength from the origin. Hence, when multiple vibrating elements are employed, the vibrating elements are preferably located at the origin of a wave created by a vibrating element. This is the stacked configuration previously discussed. Alternatively, it is preferred to that the plurality of vibrating elements are identical crystals which are in phase. For example, when vibrating elements are spaced from each other, their spacing can be represented by the formula $n+\frac{1}{2}$ wavelengths where n can be any integer. Thus one vibrating element can be spaced from another vibrating element at distances such as, for example, 0.5, 1, 1.5, and 2 wavelengths. Alternatively, for example, if 3 vibrating elements are employed, one vibrating element can be secured to a shaft, a second vibrating element can be secured ½ wavelength from the first and a third vibrating element can be secured 1 wavelength from the first vibrating element.

As mentioned above, the energy of a vibrational wave is at a minimum at $n+\frac{1}{2}$ wavelength. However, areas of maximum energy occur at points where a vibrational wave is furthest away from the axis which defines its propagation direction. Graphically speaking, assuming a wave begins at the axis which is perpendicular to the waves direction, the areas of maximum energy occur at ¼ of a wavelength from a wave's origin and at ¾ of a wavelength from the origin of a wave. Thus, maximum energy areas occur at $n+\frac{1}{4}$ wavelengths from the origin and $n+\frac{3}{4}$ wavelengths from the origin where n can be any integer. In order to subject a vibratable member to the maximum amount of energy and thereby achieve the greatest amount of particulate disruption along such an element, it is preferable to locate the vibratable member distances of $n+\frac{1}{4}$ or $n+\frac{3}{4}$ wavelengths away from the vibrating element(s). Thus, the vibratable member is preferably located at, for example, 0.25, 0.75, 1.25, and 1.75 wavelengths from a vibrating element.

In cases where the vibratable member is distanced from the vibrating element, such as those embodiments shown in FIG. 1 and FIG. 2, the means for achieving such spacing such as, for example the shaft or positioning sheaths mentioned above, is generally any elongate member suitable for propagating vibrational energy waves to the vibratable member. Generally any material capable of serving this function would be suitable for use according to the present invention. Such materials include, but are not limited to metals such as aluminum, steel, iron, titanium, alloys thereof, and the like. Cylindrical members are typically employed to space the vibratable member from the vibrating element since they are readily available.

Means for creating a standing sonic wave may comprise the vibratable member and the vibrating element because upon contacting the vibratable member, vibrational energy from the vibrating elements result in the formation of a standing sonic wave which radiates across the vibratable member. When the vibrational waves contact the vibratable member, they radiate toward the vibratable member's periphery and such waves continue to radiate as long as power is supplied to the system. As a result, a plurality of vibrational waves are created across the vibratable member. As these waves reach the ends of the vibratable member, they are reflected back. Thus, in addition to the waves being transmitted toward the edge of vibratable member, a plurality of waves are reflected back in the opposite direction. Accordingly, multiple vibrational waves travel back and forth across the vibratable member upon activation of the power supply. Eventually, these waves aggregate to establish a equilibrium wave across the vibratable member. This equilibrium wave is referred to as a "standing sonic wave".

Practically speaking, the standing sonic wave is created instantaneously upon activation of the electrical wave generator. As a result of the plurality of vibrational waves assembling to form the standing sonic wave, the standing sonic wave can have a frequency which is higher in comparison to the electrical wave output of the electrical wave generator or the vibrational wave generated by the vibrating element. Thus, the frequency of the sonic wave which contacts the test sample can be greater than the frequency of the waves which originate at the vibrating element and contact the vibratable member. The vibratable member has been found to more than double the frequency of the vibrational wave emitted by the vibrating elements.

A standing sonic wave has maximum zones of energy at $n+\frac{1}{4}$ and $n+\frac{3}{4}$ wavelength distances from the origin of the wave. In order to make efficient use of the standing sonic wave's energy to break up particulate material that may be present in a test sample, it is preferable to secure sample tubes to the vibratable member at $n+\frac{1}{4}$ or $n+\frac{3}{4}$ wavelength distances from the origin of standing sonic wave where n is any integer. It will be understood, of course, that the area on the plate where sample tubes are secured is not intended to limit the scope of the present invention, the $n+\frac{1}{4}$ and $n+\frac{3}{4}$ guidelines are merely an indication where optimum sonication has been found to occur.

The sites of maximum energy on a vibratable member can be determined using computer programs capable of performing finite element analysis whereby variables including the acoustic impedance of the plate material (a measure of the speed of sound in the material and the materials density), the plates dimensions, and the wavelength of the wave contacting the plate are entered, and areas of minimum and maximum energy across a plate are calculated. Such a program is available from Algor, Inc.; Pittsburgh, Pa.

Alternatively, the sites of minimum and maximum energy across the plate readily can be determined empirically. Specifically, prior to inputting power to the system, small particulate material such as sand, talc, silicon carbide or glass beads can be placed on the vibratable member. Upon providing the system with energy, the particulate material will migrate to areas of minimum energy. These sites represent areas having $n+\frac{1}{2}$ wavelengths from the origin of the wave wherein n is any integer and assuming the wave begins at the intersection of the vibratable member and the vibrational wave from the vibrating element. Hence, the areas between these cites represent $n+\frac{1}{4}$ wavelengths from the origin of the wave, or as previously discussed, areas of maximum energy. Accordingly, these areas are preferred sites for securing sample tubes. This method of determining areas of maximum energy is preferred because in practice, this method readily yields a accurate determination of regions of maximum and minimum energy.

Figure 3A:
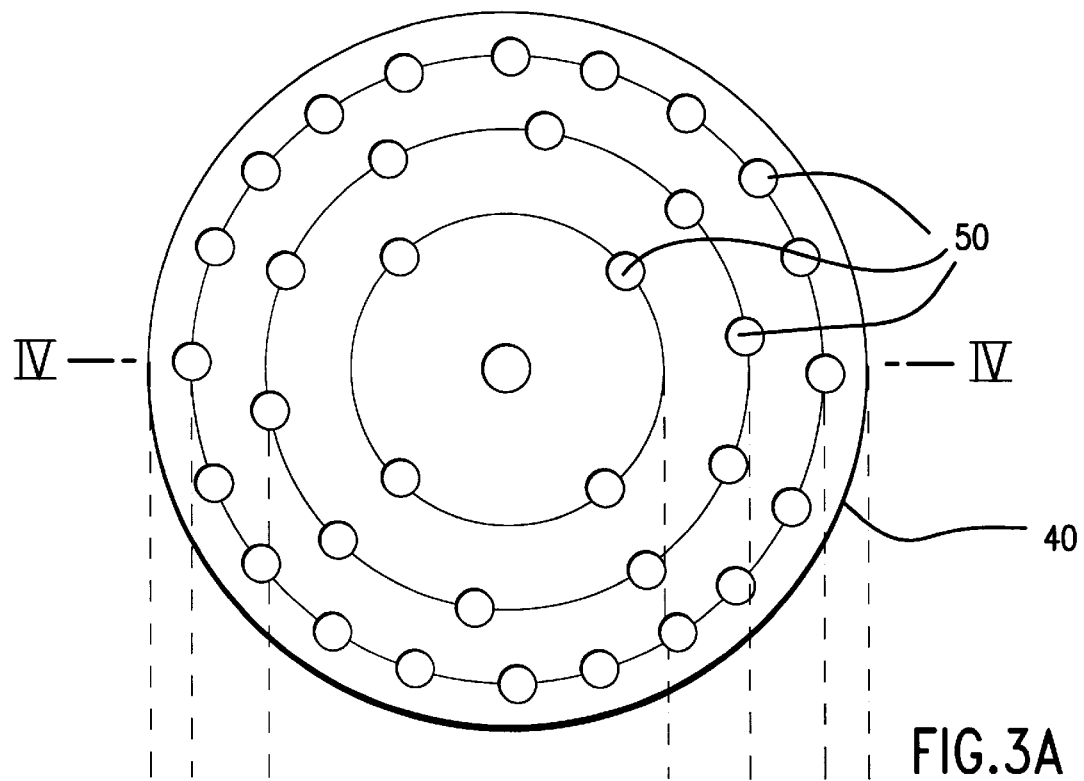
FIG. 3 is a top view of a standing sonic wave sonicator's vibratable member in the form of a plate and cross sectional view of the plate through section IV—IV.
Figure 3B:
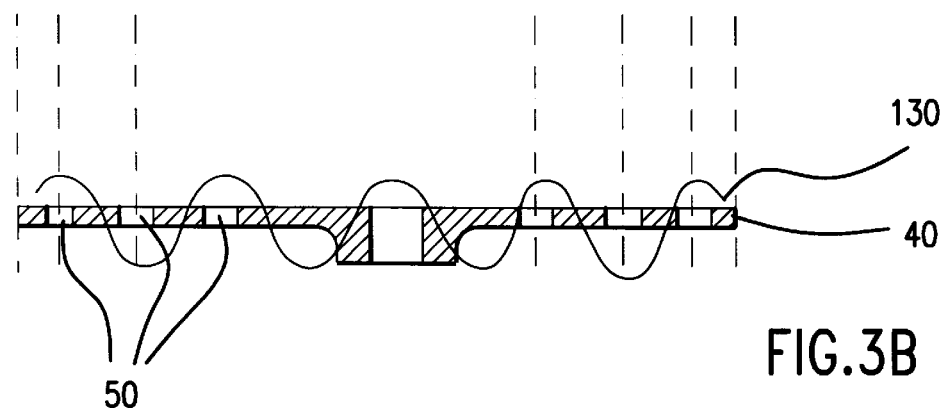

FIG. 3 illustrates a preferred method for securing sample tubes to a vibratable member in the form of a plate. FIG. 3 shows a side view and top view of a vibratable member/plate 40 with an image of a standing sonic wave 130 transposed on the side view. Apertures 50 for securing sample tubes to the plate are shown at areas where the standing sonic wave is at maximum energy. Apertures are preferred because they can be threaded, tapered or both to ensure contact between the vibratable member and the sample tubes. While apertures are preferred for securing sample tubes to a plate, other means such as resilient bands, hooks, flanges, dips, clasps, snaps and the like are suitable.

The dimensions of the vibratable member employed according to the instant invention is a matter of choice for one skilled in the art. In order to form a standing sonic wave, however, the vibratable member should be larger or overhang the vibrating element (or means for attaching the vibrating member to the vibrating element) in at least one dimension. Preferably, the vibratable member overhangs, as described above, the vibrating element or attaching means a distance of at least ½ wavelength of the wave generated by the vibrating element. Circular plates are preferred vibratable members because areas on a plate where the standing sonic wave is at maximum energy allows for practical sample placement. However, square, rectangular, cylindrical and like shapes are suitable for use as vibratable members according to the present invention.

Suitable materials for forming a vibratable member also are largely a matter of choice for one skilled in the art based upon the materials ability to form a standing sonic wave. While both elastic materials and rigid materials can form standing sonic waves, it will be understood that when rigid materials are employed to form a vibratable member, energy input into the system will be greater than when elastic materials are employed to form the vibratable member. Metals, metal alloys and polymeric materials as well as copolymers, blends or laminates, and metals deposited on polymeric material may be employed as plate materials. For example, such vibratable member materials include but are not limited to aluminum; titanium; stainless steel; polyolefins such as polypropylene and polyethylene; polyesters such as polyethylene terephthalate; styrene containing polymers such as polystyrene, styreneacrylonitrile, and acrylonitrilebutadienestyrene; polycarbonate; acrylic polymers such as polymethylmethacrylate and polyacrylonitrile; chlorine containing polymers such as polyvinylchloride and polyvinylidenechloride; acetal homopolymers and copolymers; fluorine containing polymers such as polyvinylidenefluoride and polytetrafluoroethylene; polyamides; polyetheretherketone; sulfur containing polymers such as polyphenylenesulfide and polyethersulfone; polyurethanes; and silicon containing polymers such as polydimethylsiloxane.

According to a preferred embodiment, a feedback phase tracking loop (hereinafter "tracking loop") is employed to insure the optimal performance of the standing sonic wave sonicator. As previously mentioned, the vibrating elements typically comprise piezoelectric materials which have various inherent frequencies depending upon the material's composition. When contacted with energy having a frequency that is not at this inherent frequency, the piezoelectric material exhibits impedance or resistance to the transformation of electrical energy into vibrational energy. Another factor which may cause resistance in this transformation is the weight of the sample tubes and samples which may be secured to the plate. An increase in energy supplied to the vibrating element helps counterbalance factors causing resistance. A tracking loop can be operatively coupled, such as with wires and connections, with the vibrating elements and alternating electrical wave generator or amplifier to measure the amount of resistance experienced by the vibrating element and adjust the frequency input of the electrical wave generator to counterbalance any increase in impedance.

Figure 4:
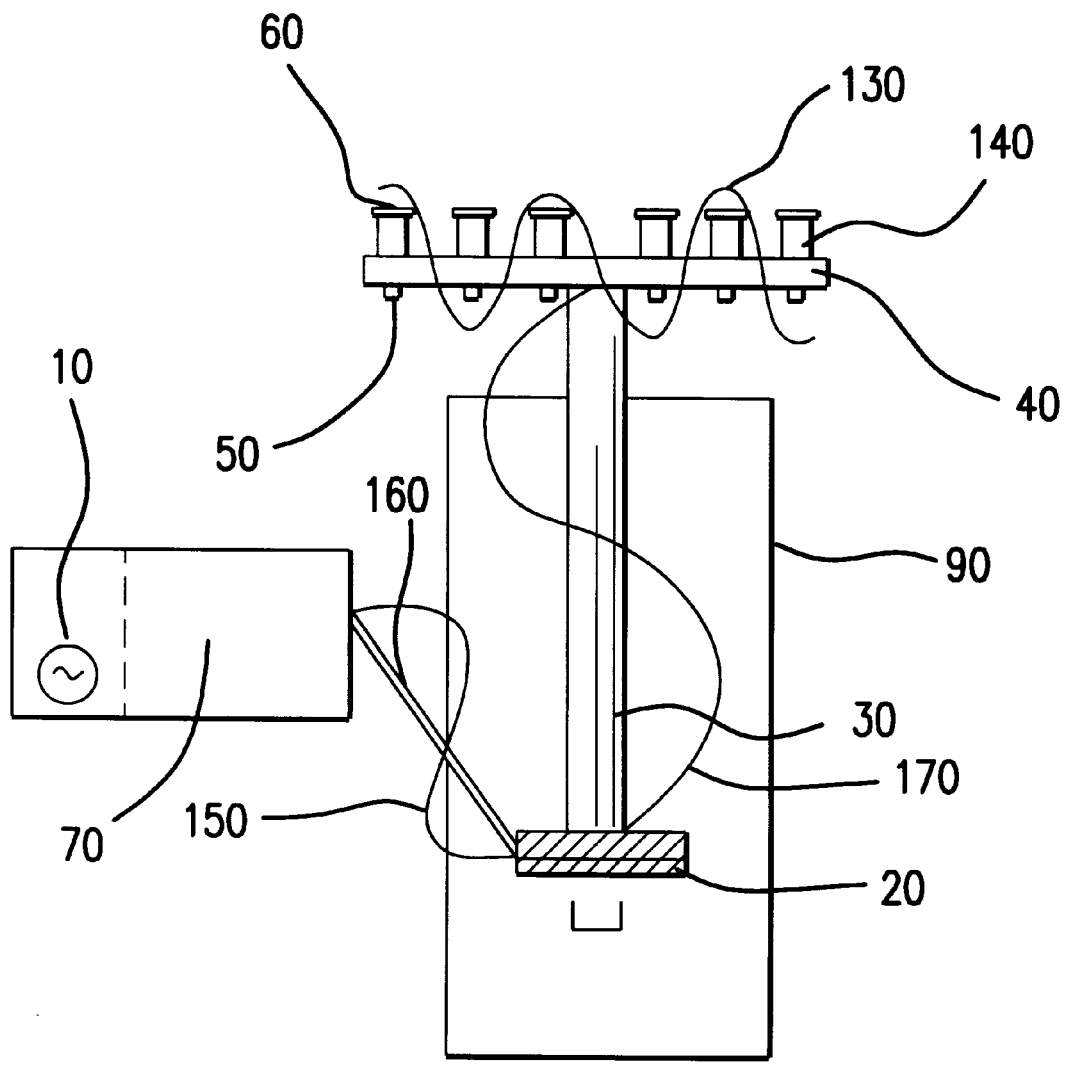
FIG. 4 illustrates an embodiment of a standing sonic wave sonicator and depicts waves propagating through such an embodiment.

The operation of the sonicator will now be discussed in concert with FIG. 4. A test sample 140 is placed in sample tube 60 and sample tube 60 is secured to vibratable member 40 using apertures 50. When activated, the electrical wave generator 10 generates electrical energy in the form of a wave having a selected frequency and amplitude. The amplitude of this wave is then increased after passing through amplifier 70. As a result, the energy of the electrical wave is increased. However, the frequency of the electrical wave remains the same. The amplified electrical wave 150 is transferred to the vibrational element 20 through, for example, wire 160 connected to amplifier 70 and vibrational element 20. Vibrational element 20 converts the electrical energy into vibrational energy and emits vibrational wave 170. Vibrational wave 170, propagates along shaft 30 toward vibratable member 40 and contacts vibratable member 40 at a point where vibratable member 40 and shaft 30 are joined. Vibrational wave 170 is converted to standing sonic wave 130 which traverses plate 40 and contacts sample tubes 60 to thereby sonicate test sample 140. After sonication is complete, typically after about 2 minutes more typically after 10 minutes, electrical wave generator 10 can be turned off which thereby dissipates the waves propagating through the system.

As previously mentioned, waves transmitted by the vibrating element contact the vibratable member and are transformed into a standing sonic wave. Sample tubes are therefore contacted with a wave that does not directly emanate from the vibrating element. Rather, the sample tubes are contacted by the standing sonic wave which is a wave created by the vibratable member and distinct from the wave created by the vibrating element. Such a wave can have a frequency greater than that emitted by the vibrating elements.

The sonicator herein provided can be employed to sonicate and thereby lyse cells such as, for example, virus or bacteria which may be present in a test sample. Upon lysing, cells release intracellular components (including nucleic acids) into the surrounding test sample. Nucleic acids released into the surrounding test sample can be detected by amplifying the released nucleic acid or fragments thereof, and detecting amplified product, if any. Methods of amplifying and detecting nucleic acid sequences are well known in the art. For example, the commercially available LCx® System (Abbott Laboratories) can be employed to amplify and detect nucleic acid sequences which are released according to the present invention. Exemplary amplification reactions which can be employed to amplify nucleic acid sequences include, but are not limited to the ligase chain reaction (LCR) described in EP-A-320,308 and EP-A-439,182 or the polymerase chain reaction (PCR) described in U.S. Pat. No. 4,683,195 and 4,683,202.

EXAMPLES

The sonicator employed for the Examples was essentially the same as that shown in FIG. 2. A function generator (Philips model PM15132; Phillips Corp.; Eindhoven, Netherlands) was used to generate a sinusoidal wave which was amplified by a model 700A1 amplifier from Amplifier Research, Souderton, Pa. The amplifier was connected to a pair of doughnut-shaped lead zirconium niobate piezoelectric vibrating elements (available from Etalon Inc., Lebanon Ind.) with wires and connections (Etalon). The vibrating elements had an inherent frequency of 29 KHz and were stacked and sandwiched between aluminum discs such that the vibrating element closest to a circular plate was 55 mm ($\lambda/4$ wavelengths) from the plate. The plate was circular piece of aluminum having an 88.9 mm diameter and a thickness of 3.1 mm. 10 circular threaded holes, 6.35 mm in diameter, were each centered at 31.75 mm from the sample plate's center to form a ring of holes around the outer periphery of the plate. Concentrically from the first 10 holes, another circle of 8 threaded holes were centered at 19.05 mm from the center of the sample plate. The plate was secured to the shaft by threading one end of the shaft and the center of the plate such that the plate and shaft could be screwed together. The shaft was secured to the aluminum disc in the same manner.

Example 1

Frequency Determination of a Standing Sonic Wave

Finely divided sand was spread across the sonicator's plate, and the electrical wave generator was activated. The sonicator's electrical wave generator was set such that the waves produced by the amplifier, and therefore transferred to the vibrating elements, had a frequency of 39 KHz and 50 watts. Upon activation of the electrical wave generator, the sand migrated to form three concentric circles across the surface of the plate. One circle of sand was located between the plate's edge and the outermost ring of sample tube holders, another was located between the rings of sample tube holders and a third circle of sand was located between the plates center and the inner-most ring of sample tube holders. The areas where the sand migrated were indicative of the areas where the standing sonic wave had minimum energy. Thus the span between the circles of sand were representative of ½ of the wavelength of the standing sonic wave generated across the plate.

The distance between the concentric circles was 13 mm. Accordingly, a full standing sonic wavelength was 0.026 m.

The speed of sound in aluminum in a transverse direction is 3040 m/second (s) and the speed of sound in aluminum in a longitudinal direction is 6420 m/s. The frequency of a wave can be calculated based upon the following formula: frequency=speed/wavelength. The frequency of the standing sonic wave across the plate was thus 3040 (m/s)/0.026 (m) for the transverse frequency. Hence, the transverse frequency (i.e. the frequency of the standing sonic wave) was 117 KHz. Accordingly, the frequency of the standing sonic wave which is the wave used to sonicate the samples, is at least more than twice the frequency of the wave inputted to the vibrating elements.

Example 2

Power Density Input/Volume of Test Sample

In this example, the power/unit volume that a sample experiences as a result of sonication with the instant sonicator was calculated. To make this determination, a volume of water and glass beads were sonicated and the temperature change in the water and glass beads was used to determine the amount of power supplied/ml.

0.5 ml of water and 0.1 ml of glass beads (150–212 micrometers diameter; Product No. 1145; Sigma Chemical Co.; St. Louis, Mo.) were added to a 1.5 ml microfuge-type sample tube (available from Sarstedt; Newton, N.C.). The sample tubes were secured to the sonicator's plate before they were sonicated for 120 seconds. The temperature of the water and beads prior to sonication was 23° C. and the temperature of the water and beads after sonication was 70° C. Based on the equation: heat (calories)=(mass)×($\Delta$ temperature)×(heat capacity-Cp), the calories of heat were calculated and convert to Joules (1 Joule=0.2388 calories). Thus, for the water, the calories absorbed was the sum of (0.5 ml)(1 gram/ml)(47° C.)(1 calorie/° C.) or 23.5 calories or 98.2 Joules. Similarly, the Joules experienced by the glass beads was calculated to be 11.8 Joules. Accordingly, the total Joules experienced by the beads and water was 110 Joules. Dividing by the time that power was being delivered to the system (120 seconds), the total watts delivered to the water and beads were 0.917 watts. Last, dividing the watts by the amount of sample (0.5 ml), it was determined that the power density experienced by the sample was 1.83 watts/ml.

Example 3

Sonication of *Mycobacterium tuberculosis* At Various Power Settings and For Various Periods In this example, nucleic acid was released from *Mycobacterium tuberculosis* strain H37Ra (Mtb) using the present sonicator. After sonicating a test sample of Mtb, LCR was run on an aliquot of the test sample to determine the extent of cell disruption caused by the sonicator.

A $4\times10^7$ colony forming unit (cfu)/ml culture of Mtb was diluted with distilled water to a concentration of 40 cfu/ml. 250 µl of the diluted culture and 100 µl of 10 mM tris (hydroxymethyl)aminomethane (Tris®), 1mM Ethylenediamine tetraacetic acid (EDTA), pH 8 buffer (TE buffer) was then placed in 1.5 ml sample tubes (Sarstedt). These tubes were then inserted into the sample tube holders by twisting the tubes through the threaded holes in the plate. Sample tubes were placed opposite each other and in cases where an odd number of tubes were to be sonicated, a blank tube containing TE buffer was placed opposite the odd sample tube. The electrical wave generator and amplifier were set to operate at a frequency of 29 KHz. Additionally, the duty rating was set at 50%. The power supplied to the plate, as well as the sonication times varied. Actual power and times are shown, along with the data from this experiment, in Table 1. The power was read as the forward power from the amplifier's panel after minimizing the reflected power from the transducer to as close to zero as possible. After sonicating the various samples, 35 µl of the sonicated mixture was added to reaction tubes for amplification of released DNA.

Released DNA was amplified using gap filling LCR essentially as set forth in U.S. Pat. No. 5,427,930 and U.S. patent application Ser. No. 08/242,403 filed May 13, 1994. The target sequence is set forth herein as SEQ. ID. NO. 1 and the probes employed to amplify the target sequence are set forth herein as SEQ. ID. NO. 2-SEQ. ID. NO. 5. Opposite ends of adjacent probes were labeled with carbazole and adamantane haptens to facilitate detection of the amplified sequences.

Amplified sequences were detected with an LCx® analyzer (Abbott Laboratories; Abbott Park, Ill.) using anti-carbazole coated microparticles and anti-adamantane antibody conjugated to alkaline phosphatase. The LCx® indicated the presence of the sequences with a rate based signal measured in counts/second/second (c/s/s).

Table 1, below, shows the results of this experiment. As shown by Table 1, the sonicator disrupted Mtb at the various powers and times tested.

TABLE 1

| Power Output (watts) | Sonication Time (minutes) | LCx ® Rate (c/s/s) | S.D. (c/s/s) |
| --- | --- | --- | --- |
| 10 | 5 | 616 | 198 |
| 10 | 10 | 1126 | 127 |
| 10 | 15 | 1322 | 42 |
| 20 | 5 | 1101 | 160 |
| 20 | 10 | 1253 | 170 |
| 20 | 15 | 1265 | 68 |
| 35 | 5 | 1286 | 157 |
| 35 | 10 | 1812 | 76 |
| 35 | 15 | 1826 | 42 |
| 50 | 5 | 1803 | 58 |
| 50 | 10 | 1821 | 45 |
| 50 | 15 | 1500 | 81 |

Example 4

Sonication with Glass Beads

The same samples, procedure and sonicator used in Example 3 were employed in this Example, except that 80 µl of glass beads (150–212 micrometers diameter—Product No. 1145; Sigma Chemical Co.; St. Louis, Mo.) were added to the sample tubes prior to sonication. The power outputs, sonication times and results for this experiment are presented in Table 2 below. As shown by Table 2, in the presence of the glass beads, the sonicator disrupted cells at the various powers and times tested.

TABLE 2

| Power Output (watts) | Sonication Time (minutes) | LCx ® Rate (c/s/s) | S.D. (c/s/s) |
| --- | --- | --- | --- |
| 10 | 5 | 1168 | 187 |
| 10 | 10 | 1352 | 46 |
| 10 | 15 | 1193 | 445 |

TABLE 2-continued

| Power Output (watts) | Sonication Time (minutes) | LCx ® Rate (c/s/s) | S.D. (c/s/s) |
| --- | --- | --- | --- |
| 20 | 5 | 1003 | 152 |
| 20 | 10 | 1138 | 117 |
| 20 | 15 | 854 | 711 |
| 35 | 5 | 1028 | 299 |
| 35 | 10 | 1775 | 70 |
| 35 | 15 | 1778 | 76 |
| 50 | 5 | 1799 | 37 |
| 50 | 10 | 1772 | 48 |
| 50 | 15 | 1801 | 54 |

Example 5

Standing Wave Sonicator, Bath Sonicator and Bead Beater Comparison

In this Example the standing sonic wave sonicator's, a bath sonicator's and a bead beater's ability to release nucleic acid from Mtb were compared.

100 μl of a 3×10$^8$ cfu/ml culture of Mtb, 80 μl of glass beads (150–212 micrometers diameter—Product No. 1145; Sigma Chemical Co.; St. Louis, Mo.), and 170 μl of TE buffer were placed in sample tubes and sonicated as in Example 3 with the standing sonic wave sonicator. However, sonication was at 50 watts for periods of 5, 10, and 30 minutes.

Bath sonication was performed with a Branson Instrument Model No. 2200 (Branson Ultrasonics Corp.; Danberry, Conn.). Samples were prepared as above for the standing sonic wave sonicator, except that 100 μl of glass beads were added to the sample tubes. The bath sonicator contained about 1.5 liters of water, preheated to 65° Celsius (C), and presonicated for 30 minutes. Sample tubes were immersed in the bath and sonicated for 20 minutes.

The Bead beater experiments were performed by mixing 100 μl of a 3×10$^8$ cfu/ml culture of Mtb with 300 μl of glass beads in sample tubes. The tubes were loaded into a sample holder and inserted into the bead beater (Nouvas Manufacturing Technology Co.; Orange, Calif.). Bead beating took place for 5 minutes.

Following the sonication and bead beating, gel electrophoresis was performed on the lysates from the various sample tubes to determine the lysed DNA sizes. An agarose gel (0.7% weight/volume) was run and ethidium bromide was used to for DNA staining. The gel demonstrated that standing wave sonication released nucleic acid from Mtb.

Example 6

Sonication Using an Electronic Phase Tracking Loop

In this Example, a standing sonic wave sonicator having a larger circular plate than that previously described and a tracking loop was used to sonicate Mtb samples. The sample plate was 127 mm in diameter and 2.38 mm thick with 20 threaded holes drilled 53.7 mm from the center of the plate and substantially equidistant from each other.

This standing wave sonicator's ability to sonicate Mtb was compared to other methods of cell lysis including bath sonication (as in Example 5), bead beating (as in Example 5) and boiling. All methods were tested with equal initial concentrations of Mtb (approximately 1 cfu/ml). Prior to sonication with the standing sonic wave sonicator, the Mtb cells were centrifuged and the resulting pellet was resuspended in TE buffer.

Bath sonication and bead beating were performed as described in Example 5. Standing wave sonication took place for 5 minutes at a frequency of 34 KHz and 100 watts of power. The duty cycle was set at 50%. Samples were placed in boiling water for 15 minutes according to the boiling method of cell lysis.

After lysis, released nucleic acid was amplified and detected in the manner described in Example 3. The results from the various methods are shown below in Table 4. Table 4 shows the results from the standing wave sonication, Table 5 shows the results from the bead beating, and Table 6 shows the results from the bath sonication. The average LCx® rate for the boiling method of lysis was 292 with a standard deviation (S.D.) of 121.

As demonstrated by the various tables, standing sonic wave sonication yielded LCx® rates comparable to the other methods of cell lysis.

TABLE 4

| Tube | LCx ® Rate c/s/s, Run I | S.D. | LCx ® Rate c/s/s, Run II | S.D. |
| --- | --- | --- | --- | --- |
| 1 | 1222 | 110 | 1118 | 163 |
| 2 | 1137 | 115 | 1116 | 111 |
| 3 | 1266 | 106 | 1223 | 124 |
| 4 | 1302 | 174 | 1141 | 50 |
| 5 | 1183 | 45 | 1167 | 115 |
| 6 | 1333 | 117 | 1136 | 113 |
| 7 | 1279 | 108 | 1222 | 76 |
| 8 | 1065 | 14 | 1098 | 37 |
| 9 | 1082 | 193 | 890 | 208 |
| 10 | 1263 | 101 | 1090 | 143 |
| 11 | 1189 | 92 | 1255 | 67 |
| 12 | 1188 | 90 | 1277 | 42 |
| 13 | 1210 | 2 | 1196 | 44 |
| 14 | 1142 | 91 | 1232 | 59 |
| 15 | 1115 | 162 | 1109 | 33 |
| 16 | 1087 | 130 | 1047 | 98 |
| 17 | 1177 | 93 | 1147 | 70 |
| 18 | 1055 | 21 | 1182 | 98 |
| 19 | 1247 | 90 | 1171 | 67 |
| 20 | 1125 | 54 | 1310 | 62 |

TABLE 5

| LCx ® Rate (c/s/s) | S.D. |
| --- | --- |
| 724 | 100 |
| 838 | 232 |
| 657 | 71 |

TABLE 6

| LCx ® Rate | S.D. |
| --- | --- |
| 520 | 57 |
| 463 | 281 |
| 381 | 322 |

Example 7

Standing Wave Sonication with a Square Plate

Figure 5:
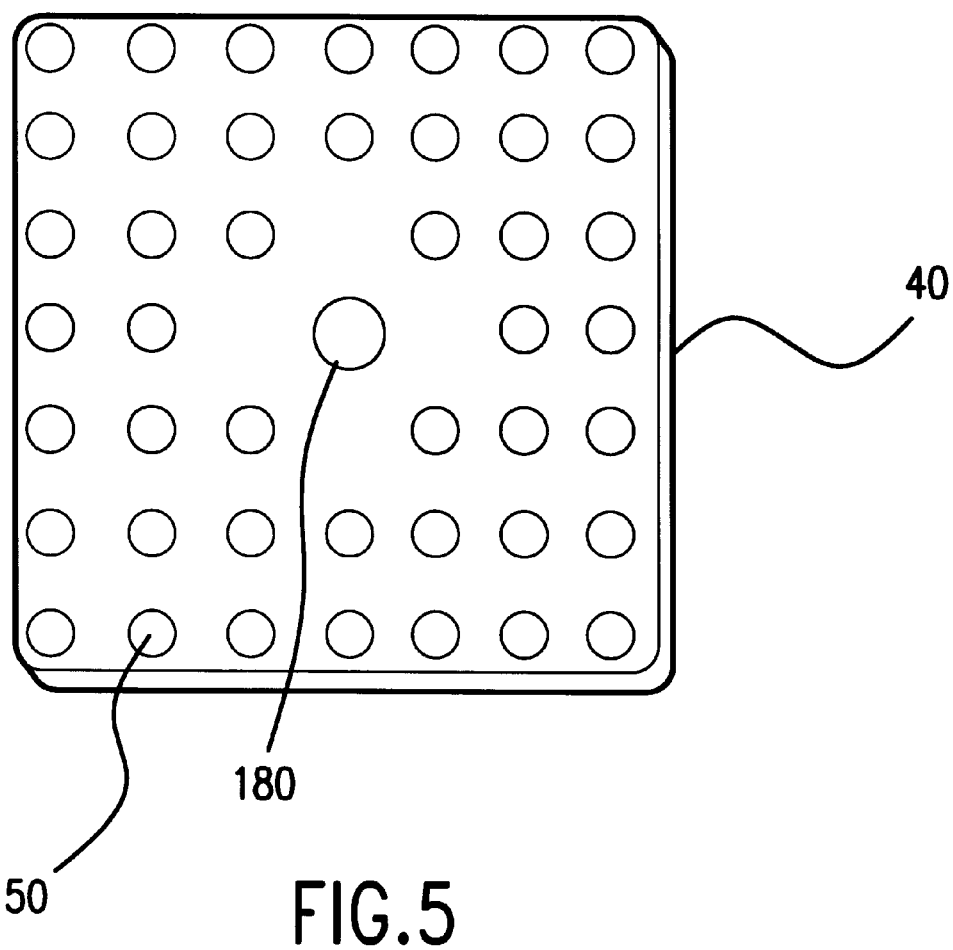
FIG. 5 is a top view of a plate which can be employed as a vibratable member which can be transversley secured to a vibrating element according to the present invention.

According to this Example a standing sonic wave sonicator equipped with 127 mm×127 mm×3.18 mm square plate was used to sonicate Mtb. Threaded holes 50 were drilled in plate 40 in the pattern shown in FIG. 5 where the site of the plate and shaft connection 180 is also shown. Sample preparation, sonication and nucleic acid detection procedures set forth in Example 3 were also employed in this Example. Table 7 presents the results obtained for 40 samples sonicated in this manner. As shown by Table 7, a standing sonic wave sonicator equipped with a square plate effectively disrupted Mtb cells.

TABLE 7

| Sample # | LCx ® Rate c/s/s | Sample # | LCx ® Rate c/s/s |
|---|---|---|---|
| 1  | 2353 | 23 | 2383 |
| 2  | 2473 | 24 | 2122 |
| 3  | 2355 | 25 | 2483 |
| 4  | 2407 | 26 | 2466 |
| 5  | 2451 | 27 | 2450 |
| 6  | 2678 | 28 | 2030 |
| 7  | 2716 | 29 | 2486 |
| 8  | 2564 | 30 | 2263 |
| 9  | 2463 | 31 | 2370 |
| 10 | 2532 | 32 | 2294 |
| 11 | 2467 | 33 | 2357 |
| 12 | 2196 | 34 | 2410 |
| 13 | 2179 | 35 | 2074 |
| 14 | 2320 | 36 | 1780 |
| 15 | 2274 | 37 | 2354 |
| 16 | 2388 | 38 | 2430 |
| 17 | 2120 | 39 | 2417 |
| 18 | 2329 | 40 | 1144 |
| 19 | 2303 | 41 | 2590 |
| 20 | 2046 | 42 | 2830 |
| 21 | 2490 | 43 | 2489 |
| 22 | 2550 | 44 | 2520 |

Example 8

Standing Wave Sonication of Clinical Samples

Clinical samples from patients suspected of being infected with Mtb were employed in this example instead of the avirulent H37Ra Mtb strain. Sputum samples were obtained from 83 patients of Orange County Medical Center, Orange County, Calif. Equal volumes of sample and a fresh solution comprising 1% N-acetyl cystein, 2% sodium hydroxide (NaOH) and 1.45% sodium citrate were mixed and allowed to stand for 20 minutes. Approximately 40 ml of sodium phosphate buffer (67 mM) was then added to the diluted samples before they were centrifuged for 15 minutes at 3000 g. The resulting pellet was resuspended in sodium phosphate buffer (67 mM) containing 0.2% bovine serum albumin and the resuspended pellet was neutralized with hydrochloric acid (HCl). Part of each sample was used for cell culturing of Mtb, a second part was used for acid fast strain (AFS), and a third part (375 $\mu$l) was used for the LCR amplification. The portion used for LCR amplification was diluted in 1 ml of TE buffer and centrifuged for 20 minutes at 3000×g. The resulting pellet was resuspended in 250 $\mu$l of TE buffer, and 30 $\mu$l of glass beads (150–212 micrometers diameter—Product No. 1145; Sigma Chemical Co.; St. Louis, Mo.) were added to the sample tubes before they were loaded into the sample holders of the standing wave sonicator employed in Example 1. All samples that were sonicated, were sonicated for 10 minutes, at a power of 50 watts, a frequency of 34 KHz, and a duty rating of 50%. 25 $\mu$l of the sonicated samples was amplified using LCR as in Example 3 and detected as in Example 3. Table 8 shows the results obtained from 8 samples using the cell culture, AFS and LCR based detection of Mtb. The remaining samples were negative for Mtb by all methods.

TABLE 8

| Sample # | Culture (Colony Count) | LCx ® Rate (c/s/s) | AFS Index |
|---|---|---|---|
| 1 | confluent | 2232 | 2+ |
| 2 | 10–50 | 2275 | 1+ |
| 3 | 200–300 | 2000 | 1+ |
| 4 | 1–10 | 1895 | 1+ |
| 5 | 10–50 | 1000 | negative |
| 6 | negative | 1200 | negative |
| 7 | negative | 606 | negative |
| 8 | negative | 451 | negative |

The AFS Index was based upon Conventions from the American Thoracic Society, "Diagnostic Standards and Classifications of Tuberculosis", Am. Rev. Respir. Dis., 1990; 142:725–735. According to this index, a value of "1+" indicates the presence of Mtb and a value of "2+" indicates a greater Mtb load than the 1+ value. According to this method of Mtb detection, 4 samples were positive.

The culture colony counts ranged from confluency to negative. Where it was possible to count the individual colonies in culture, those counts were represented and placed in the ranges shown in Table 8. According to this method of Mtb detection, 5 samples were positive. All samples determined to be positive by this method were determined to be contaminated with Mtb. The mycobacterium species was determined by a Accuprobe® Mtb probe kit (Gen-Probe Inc., San Diego, Calif.).

The standing sonic wave sonicator and LCR amplification of an Mtb target sequence indicated that 8 samples were positive for Mtb. Additionally, this method detected Mtb in all samples which were positive by either culture or AFS. Patients whose samples were positive by this method of Mtb detection and no others were treated for Mtb infection. Hence, the standing sonic wave sonicator was effective at releasing nucleic acid from Mtb.

While the invention has been described in detail and with reference to specific embodiments, it will be apparent to one skilled in the art that various changes and modifications may be made to such embodiments without departing from the spirit and scope of the invention. Additionally, all patents and publications mentioned above are herein incorporated by reference.

What is claimed is:

1. A device for sonicaing a sample comprising:
   (a) an electrical wave generator;
   (b) a vibrating element electrically connected to said electrical wave generator; and
   (c) a vibratable member transversely secured to said vibrating element wherein upon activation of said device, said vibratable member generates a standing sonic wave and wherein said vibratable member comprises means for securing samples which are located on said vibrating member at zones of maximum energy.

2. The device of claim 1 further comprising an amplifier electrically connected with said electrical wave generator and said vibrating element.

3. The device of claim 2 further comprising an amplifier electrically connected to said electrical wave generator and a feedback phase tracking loop operatively coupled with said amplifier and said vibrating element.

4. The device of claim 1 further comprising a second vibrating element stacked on said vibrating element.

5. The device of claim 1 wherein said vibrating element is secured to said vibratable member with a shaft wherein said vibrating element is secured near a first end of said shaft and said vibratable member is secured near a second end of said shaft.

6. The device according to claim 1, wherein the standing sonic wave has maximum zones of energy at n+¼ and n+¾ wavelength distances from the origin of the wave.

7. A method of sonication comprising the steps of:
   (a) converting an electrical energy wave into a vibrational energy wave with a vibrating element;
   (b) contacting a vibratable member with said vibrational energy wave to generate a standing sonic wave across said vibratable member; and
   (c) contacting a test sample with said standing sonic wave, wherein said vibratable member is transversely secured to said vibrating element and said vibratable member comprises means for securing said test sample which are located on said vibrating member at zones of maximum energy.

8. The method of claim 7 wherein said vibratable member is a circular plate.

9. The method of claim 7 wherein said standing sonic wave has a frequency greater than about 100 KHz.

10. The method according to claim 7, wherein the standing sonic wave has maximum zones of energy at n+¼ and n+¾ wavelength distances from the origin of the wave.

11. A method of generating a standing sonic wave comprising propagating vibrational energy through a vibrating shaft to a vibratable member to thereby generate a standing sonic wave across said vibratable member, wherein said vibratable member is transversely secured to said vibrating shaft and said vibratable member comprises means for securing samples which are located on said vibrating member at zones of maximum energy.

12. The method of claim 11 further comprising the step of exposing particulate material to said standing sonic wave.

13. The method according to claim 11, wherein the standing sonic wave has maximum zones of energy at n+¼ and n+¾ wavelength distances from the origin of the wave.

* * * * *

UNITED STATES PATENT AND TRADEMARK OFFICE
CERTIFICATE OF CORRECTION

PATENT NO. : 6,071,480
DATED : June 6, 2000
INVENTOR(S) : Folim G. Halaka

It is certified that error appears in the above-indentified patent and that said Letters Patent is hereby corrected as shown below:

Col. 6, line 36
  replace "dips"
  with --clips--.
Col. 13, line 57
  replace "strain"
  with --stain--.

Signed and Sealed this

Tenth Day of April, 2001

*Attest:*

NICHOLAS P. GODICI

*Attesting Officer*  *Acting Director of the United States Patent and Trademark Office*